(12) United States Patent
Vega

(10) Patent No.: US 6,475,156 B1
(45) Date of Patent: Nov. 5, 2002

(54) APPARATUS FOR THE DIAGNOSIS OR TREATMENT OF RESPIRATORY SLEEP DISORDERS AND OPERATING PROCESS

(75) Inventor: Enrique Vega, Paris (FR)

(73) Assignee: Taema, Antony (FR)

( * ) Notice: Subject to any disclaimer, the term of this patent is extended or adjusted under 35 U.S.C. 154(b) by 27 days.

(21) Appl. No.: 09/592,868

(22) Filed: Jun. 13, 2000

(30) Foreign Application Priority Data

Jun. 14, 1999 (FR) .............................. 99 07489

(51) Int. Cl.[7] ................................. A61B 5/08
(52) U.S. Cl. .................. 600/529; 600/538; 128/204.18; 128/204.23
(58) Field of Search ................ 600/529, 532, 600/534, 538, 531, 533, 537, 539; 128/200.12–200.23, 200.24, 204.18, 204.21, 204.23, 204.25

(56) References Cited

U.S. PATENT DOCUMENTS

| | | | |
|---|---|---|---|
| 4,905,687 A | | 3/1990 | Ponkala |
| 5,558,099 A | * | 9/1996 | Bowman et al. ............ 600/538 |
| 5,560,371 A | * | 10/1996 | Carvalho da Silva ....... 600/538 |
| 5,740,795 A | * | 4/1998 | Brydon .................. 128/204.21 |
| 6,155,985 A | * | 12/2000 | Ruton ......................... 600/529 |
| 6,179,784 B1 | * | 1/2001 | Daniels et al. .......... 600/529 X |
| 6,190,328 B1 | * | 2/2001 | Ruton et al. ................. 600/532 |
| 6,237,593 B1 | * | 5/2001 | Brydon .................. 128/204.22 |

FOREIGN PATENT DOCUMENTS

| | | |
|---|---|---|
| EP | 0 656 216 A2 | 12/1994 |
| WO | WO 97/28838 | 8/1997 |
| WO | WO 98/12965 | 4/1998 |

* cited by examiner

*Primary Examiner*—Kevin Shaver
*Assistant Examiner*—Navin Natnithithadha
(74) *Attorney, Agent, or Firm*—Young & Thompson

(57) ABSTRACT

The apparatus includes a motorized turbine making it possible to deliver a stream of respiratory gas under variable or constant pressure into a patient circuit linked to a user. In the process an image of the respiratory flow rate of the patient is determined on the basis of the variations in the electric current consumed by the turbine. An image of the respiratory volume of the patient is determined by integrating the image of the respiratory flow rate of the patient. The moving average of the image of the respiratory volume of the patient is determined over n respiratory cycles and a respiratory flow rate restriction is determined, below that of an apnea or a hypopnea, representative of an event of ORE type.

15 Claims, 2 Drawing Sheets

APPARATUS FOR THE DIAGNOSIS OR TREATMENT OF RESPIRATORY SLEEP DISORDERS AND OPERATING PROCESS

FIELD OF THE INVENTION

The present invention relates to a process for operating or for controlling an artificial ventilation apparatus making it possible to diagnose or to treat sleep disorders of ORE type, during which a patient is subject to restrictions of his respiratory volume which are smaller than those occurring during a period of apnea or of hypopnea, but nevertheless of sufficient concern to require treatment, as well as to such an apparatus.

BACKGROUND OF THE INVENTION

At present, numerous apparatuses for the artificial ventilation of a patient make it possible to ensure effective detection of certain respiratory sleep disorders, namely apneas or hypopneas.

An apnea is defined as a sleep disorder which is characterized in an individual by stoppage of respiratory activity for a variable period of time during his sleep, that is to say a reduction of more than 90% in the amplitude of the normal respiratory flow rate of this individual.

FIG. 1 depicts a respiratory cycle in a patient subject to sleep apnea type disorders. As may be seen, between times t1 and t2, the respiratory volume decreases considerably relative to the normal respiratory volume (100%), reaching a respiratory volume of the order of or close to 0%, that is to say periods during which the patient is not breathing, i.e. is in a period of apnea.

Additionally, a hypopnea is in turn defined as a sleep disorder which is characterized in an individual by a 50% decrease in the amplitude of the respiratory flow rate of this individual for a variable period of time during his sleep.

FIG. 2 depicts a respiratory cycle in a patient subject to sleep hypopnea type disorders. As may be seen, between times t1 and t2, the respiratory volume decreases sharply relative to the normal respiratory volume (100%), reaching a respiratory volume of the order of or less than 50% of the normal volume, that is to say periods during which the patient is not breathing fully, i.e. is in a period of hypopnea. However, during the periods of hypopnea, the respiratory volume decreases much less than in periods of apnea.

There are nowadays numerous methods and apparatuses making it possible to diagnose or to treat these two types of respiratory disorders and, in this regard, mention may be made in particular of the documents U.S. Pat. Nos. 5,245,995, 5,148,802, 5,199,424, 4,655,213, 5,335,654, 5,353,788, 5,458,137 and EP-A-505232.

However, recent studies have shown the existence of respiratory events of a third type giving rise to respiratory sleep disorders in an individual affected thereby, namely respiratory events which do not entail a reduction of from 50% to almost 100% of the respiratory flow rate, as in the case of hypopnea or apnea, but which give rise, on the other hand, to a reduction in respiratory volume for the duration of the event, followed by a resumption of respiration and very slight arousal of the individual at the end of the event.

During the resumption of respiration and the very slight arousal, one witnesses a considerable increase in the volume of respiratory gas inhaled by the individual.

Such respiratory events correspond to periods of flow restriction and are referred to as events of the ORE type, standing for Other Respiratory Events, thereby making it possible to distinguish them from apneas and hypopneas.

FIG. 3 depicts a respiratory cycle in a patient subject to sleep disorders of ORE type. As may be seen, in this case, between times t1 and t2, the respiratory volume decreases slightly relative to the normal respiratory volume (100%), reaching a respiratory volume which is still greater than 50% of the normal volume, that is to say during these periods of restriction in respiration, the respiratory volume decreases less than in periods of hypopnea, thus rendering these disorders of ORE type more difficult to detect or to diagnose.

Now it is vital to be able to ensure effective detection of these periods of flow restriction corresponding to events of the ORE type if one wishes to carry out diagnosis and/or correct treatment of the respiratory sleep disorders of an individual.

Therefore, the problem which arises is that of proposing an apparatus capable of carrying out effective detection of the periods of flow restriction corresponding to events of the ORE type in an individual suffering from respiratory sleep disorders, in such a way that the doctor or the like can subsequently carry out effective diagnosis of such ORE disorders and prescribe an appropriate treatment.

SUMMARY OF THE INVENTION

An object of the present invention is to provide an apparatus for the diagnosis or the treatment of respiratory sleep disorders of a user.

Another object of the present invention is to provide a process for operating an apparatus for the diagnosis or the treatment of respiratory sleep disorders of a user.

It is precisely the periods of sleep disorders of ORE type, during which the patient experiences restrictions in respiratory volume which are smaller than those occurring during a period of apnea or of hypopnea, that the present invention makes it possible to detect effectively, in such a way as to subsequently allow a doctor, practitioner or the like to deduce, from the data gathered, a reliable cue which can be utilized to allow a diagnosis to be made and allow the implementation of effective treatment of the patient.

BRIEF DESCRIPTION OF THE DRAWINGS

The present invention will be described in greater detail with regard to the appended drawings in which.

DETAILED DESCRIPTION OF THE INVENTION

Figure 1:
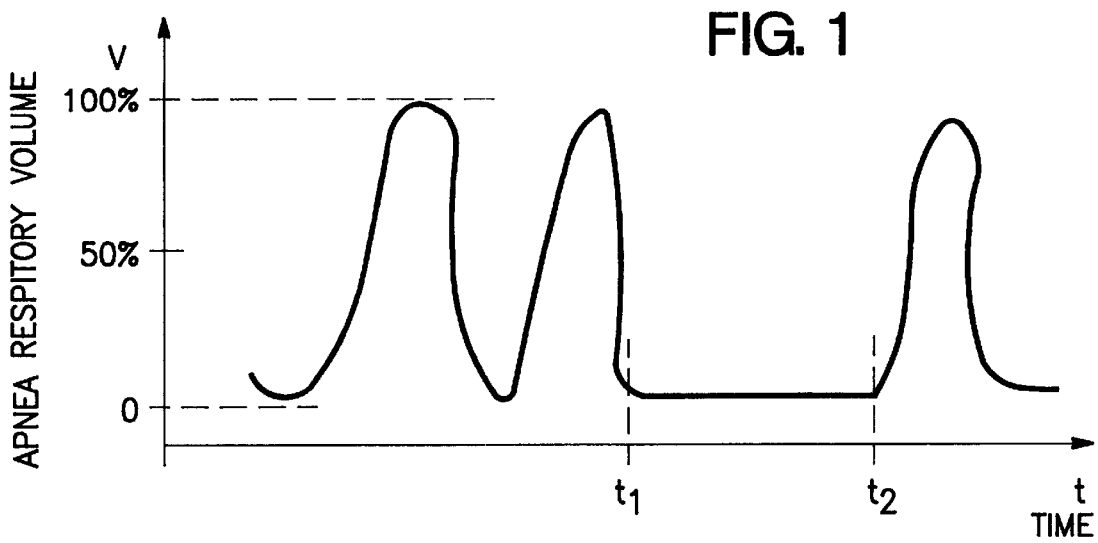
FIGS. 1 to 3 given by way of nonlimiting illustration show the three types of sleep disorders which may be observed in patient.
Figure 2:
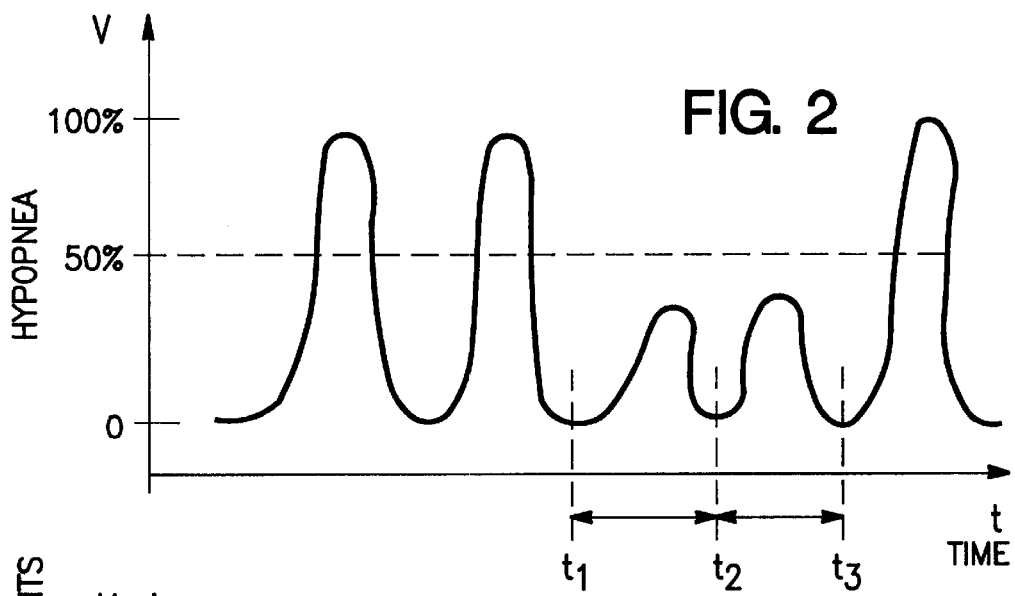
Figure 3:
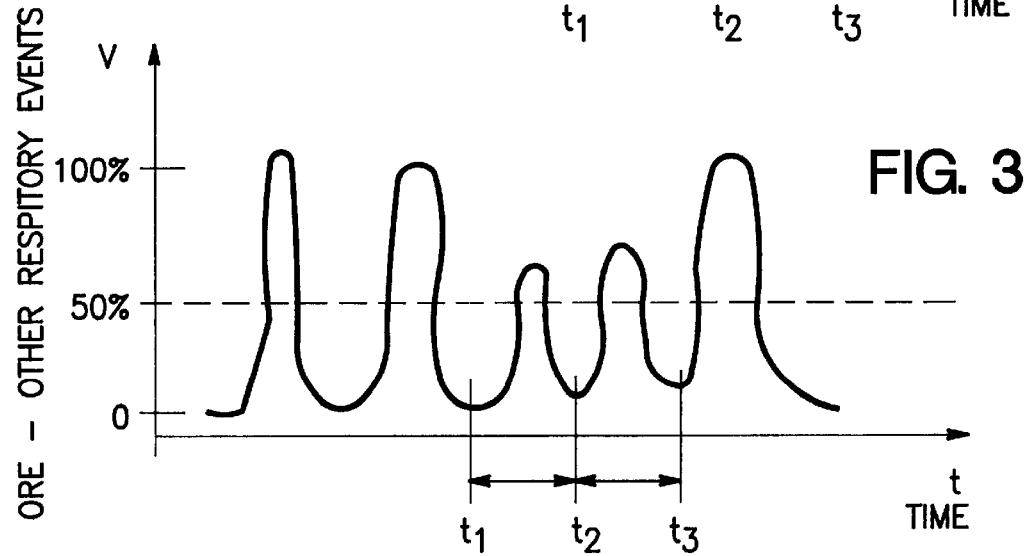
Figure 4:
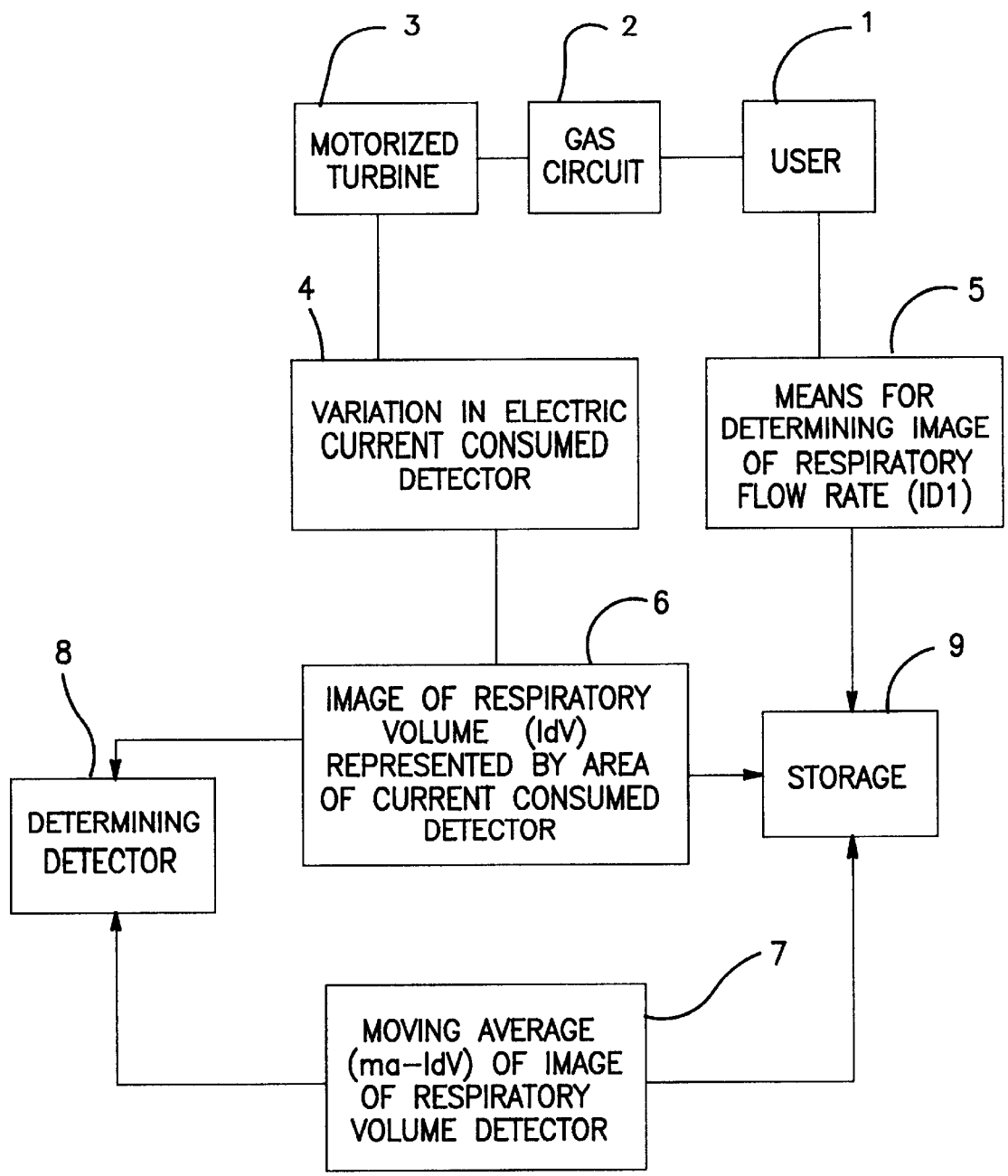
FIG. 4 is a schematic diagram of an apparatus according to the invention.

With reference to FIG. 4, the invention relates to an apparatus for the diagnosis or the treatment of the respiratory sleep disorders of a user 1 capable of operating according to an operating process according to the invention, said apparatus comprising a gas circuit 2 capable of being linked to said user and at least one motorized turbine 3 making it possible to deliver a stream of respiratory gas under variable or constant pressure into at least said gas circuit, comprising:

means 4 of detecting and/or of monitoring the variations in the electric current consumed by the turbine during at least part of at least one given respiratory cycle;

means 5 of determining an image of the respiratory flow rate (IdD) of the patient;

means 6 of determining an image of the respiratory volume (IdV) of the patient as represented by the area (Acc) of the current consumed during at least part of said at least one given respiratory cycle, comprising means of integrating the image of the respiratory flow rate of the patient (IdD) so as to obtain said area (Acc) of the current consumed;

means 7 of determining the moving average (ma-IdV) of the image of the respiratory volume of the patient over the n respiratory cycles which preceded said at least one given respiratory cycle, with n >5;

means 8 of determining at least one cue representative of at least one respiratory flow rate restriction during at least said given respiratory cycle (i) by comparing the image of the respiratory volume (IdV) with the moving average (ma-IdV) of the image of the respiratory volume, and/or (ii) by calculating the ratio between the image of the respiratory volume (IdV) and the area (Asp) of a preset pure sine and/or the area (Asc) of a preset square signal; and means 9 of storing and/or displaying and/or printing at least one respiratory flow rate cue and/or at least one datum chosen from the group formed by the image of the respiratory flow rate (IdD), the image of the respiratory volume (IdV), and the moving average (ma-IdV) of the image of the respiratory volume.

According to case, the apparatus of the invention can comprise one or more of the following characteristics:

the means 4 of detecting and/or of monitoring the variations in the electric current consumed by the turbine make it possible to determine an image of the respiratory flow rate (IdD) and/or to determine an image of the respiratory volume (IdV) over at least part of at least two successive given respiratory cycles, preferably over three or four successive given respiratory cycles;

the means 7 of determining the moving average make it possible to determine the moving average (ma-IdV) of the image of the respiratory volume of the patient over the n respiratory cycles which preceded said at least one given respiratory cycle, with n >10, preferably n lies between 15 and 40, preferably still between 20 and 30;

the means 8 of determining at least one cue representative of at least one respiratory flow rate restriction make it possible to subtract a value of moving average (ma-IdV) of the image of the respiratory volume, as determined by the means of determining the moving average, from the value of the area (Acc) of the current consumed corresponding to the image of the respiratory volume (IdV) as determined by the means of determining an image of the respiratory volume (IdV).

The present invention also relates to a process for operating an apparatus for the diagnosis or the treatment of the respiratory sleep disorders of a user, as depicted in FIG. 4, said apparatus comprising at least one motorized turbine making it possible to deliver a stream of respiratory gas under variable or constant pressure into at least one patient circuit capable of being linked to said user, the process comprising the steps of:

(a) determining an image of the respiratory flow rate (IdD) of the patient by detecting and/or monitoring the variations in the electric current consumed by the turbine during at least part of at least one given respiratory cycle;

(b) determining an image of the respiratory volume (IdV) of the patient by integrating the image of the respiratory flow rate of the patient (IdD) so as to obtain the area (Acc) of the current consumed during at least part of said at least one given respiratory cycle;

(c) determining the moving average (ma-IdV) of the image of the respiratory volume of the patient over the n respiratory cycles which preceded said at least one given respiratory cycle, with n >5;

(d) determining at least one cue representative of at least one respiratory flow rate restriction during at least said given respiratory cycle:
  (i) by comparing the image of the respiratory volume (IdV) as determined in step (b) with the moving average (ma-IdV) of the image of the respiratory volume as determined in step (c), and /or
  (ii) by calculating the ratio between the image of the respiratory volume (IdV) as determined in step (b) and the area (Asp) of a preset pure sine and/or the area (Asc) of a preset square signal;

(e) storing and/or displaying and/or printing at least one cue as determined in step (d).

According to case, the process of the invention can comprise one or more of the following characteristics:

in step (a), an image of the respiratory flow rate (IdD) is determined and/or in step (b), an image of the respiratory volume (IdV) is determined over at least part of at least two successive given respiratory cycles, preferably over three or four successive given respiratory cycles;

in step (c), the moving average (ma-IdV) of the image of the respiratory volume of the patient is determined over the n respiratory cycles which preceded said at least one given respiratory cycle, with n >10, preferably n lies between 15 and 40, preferably still between 20 and 30;

it furthermore comprises at least one step of storing and/or displaying and/or printing at least one datum chosen from the group formed by the image of the respiratory flow rate (IdD), the image of the respiratory volume (IdV), and the moving average (ma-IdV) of the image of the respiratory volume;

in step (d), a value of moving average (ma-IdV) of the image of the respiratory volume as determined in step (c) is subtracted from the value of the area (Acc) of the current consumed corresponding to the image of the respiratory volume (IdV) as determined in step (b).

More generally, the vagaries of the respiration of a patient in the sleep phase may sometimes lead to respiratory flow rate reductions or restrictions which are not disorders of the ORE type or other artifacts which could lead to erroneous diagnoses.

To remedy this, it may be desirable to set criteria for detecting and/or discriminating artifacts of this type, for example an overly short duration of the inhalation or exhalation time, an overly small quantity of inhalatory or exhalatory flux, etc.

What is claimed is:

1. A process for operating an apparatus for the diagnosis or the treatment of the respiratory sleep disorders of a user, said apparatus comprising at least one motorized turbine making it possible to deliver a stream of respiratory gas under variable or constant pressure into at least one patient circuit capable of being linked to said user, comprising the steps of:

(a) determining an image of the respiratory flow rate (IdD) of the patient by detecting and/or monitoring the variations in the electric current consumed by the turbine during at least part of at least one given respiratory cycle;

(b) determining an image of the respiratory volume (IdV) of the patient by integrating the image of the respiratory flow rate of the patient (IdD) so as to obtain the area (Acc) of the current consumed during at least part of said at least one given respiratory cycle;

(c) determining the moving average (ma-IdV) of the image of the respiratory volume of the patient over the n respiratory cycles which preceded said at least one given respiratory cycle, with n>5;

(d) determining at least one cue representative of at least one respiratory flow rate restriction during at least said given respiratory cycle:

(i) by comparing the image of the respiratory volume (IdV) as determined in step (b) with the moving average (ma-IdV) of the image of the respiratory volume as determined in step (c), and/or (ii) by calculating the ratio between the image of the respiratory volume (IdV) as determined in step (b) and the area (Asp) of a preset pure sine and/or the area (Asc) of a preset square signal;

(e) storing and/or displaying and/or printing at least one cue as determined in step (d).

2. The process as claimed in claim 1, wherein in step (a), an image of the respiratory flow rate (IdD) is determined and/or in step (b), an image of the respiratory volume (IdV) is determined over at least part of at least two successive given respiratory cycles.

3. The process as claimed in claim 2, wherein in step (a), an image of the respiratory flow rate (IdD) is determined and/or in step (b), an image of the respiratory volume (IdV) is determined over at least part of over three or four successive given respiratory cycles.

4. The process as claimed in claim 1, wherein in step (c), the moving average (ma-IdV) of the image of the respiratory volume of the patient is determined over the n respiratory cycles which preceded said at least one given respiratory cycle, with n>10.

5. The process as claimed in claim 4, wherein in step (c), the moving average (ma-IdV) of the image of the respiratory volume of the patient is determined over the n respiratory cycles which preceded said at least one given respiratory cycle, with n between 15 and 40.

6. The process as claimed in claim 5, wherein in step (c), the moving average (ma-IdV) of the image of the respiratory volume of the patient is determined over the n respiratory cycles which preceded said at least one given respiratory cycle, with n between 20 and 30.

7. The process as claimed in claim 1, which furthermore comprises at least one step of storing and/or displaying and/or printing at least one datum chosen from the group formed by:

the image of the respiratory flow rate (IdD), the image of the respiratory volume (IdV), and the moving average (ma-IdV) of the image of the respiratory volume.

8. The process as claimed in claim 1, wherein in step (d), a value of moving average (ma-IdV) of the image of the respiratory volume as determined in step (c) is subtracted from the value of the area (Acc) of the current consumed corresponding to the image of the respiratory volume (IdV) as determined in step (b).

9. An apparatus for the diagnosis or the treatment of the respiratory sleep disorders of a user capable of operating according to an operating process as claimed in claim 1, said apparatus comprising a gas circuit capable of being linked to said user and at least one motorized turbine making it possible to deliver a stream of respiratory gas under variable or constant pressure into at least said gas circuit, comprising:

means of detecting and/or of monitoring the variations in the electric current consumed by the turbine during at least part of at least one given respiratory cycle;

means of determining an image of the respiratory flow rate (IdD) of the patient;

means of determining an image of the respiratory volume (IdV) of the patient as represented by the area (Acc) of the current consumed during at least part of said at least one given respiratory cycle, comprising means of integrating the image of the respiratory flow rate of the patient (IdD) so as to obtain said area (Acc) of the current consumed;

means of determining the moving average (ma-IdV) of the image of the respiratory volume of the patient over the n respiratory cycles which preceded said at least one given respiratory cycle, with n>5;

means of determining at least one cue representative of at least one respiratory flow rate restriction during at least said given respiratory cycle (i) by comparing the image of the respiratory volume (IdV) as determined in step (b) with the moving average (ma-IdV) of the image of the respiratory volume as determined in step (c), and/or (ii) by calculating the ratio between the image of the respiratory volume (IdV) as determined in step (b) and the area (Asp) of a preset pure sine and/or the area (Asc) of a preset square signal; and means of storing and/or displaying and/or printing at least one respiratory flow rate cue and/or at least one datum chosen from the group formed by the image of the respiratory flow rate (IdD), the image of the respiratory volume (IdV), and the moving average (ma-IdV) of the image of the respiratory volume.

10. The apparatus as claimed in claim 9, wherein the means of detecting and/or of monitoring the variations in the electric current consumed by the turbine make it possible to determine an image of the respiratory flow rate (IdD) and/or to determine an image of the respiratory volume (IdV) over at least part of at least two successive given respiratory cycles.

11. The apparatus as claimed in claim 10, wherein the means of detecting and/or of monitoring the variations in the electric current consumed by the turbine make it possible to determine an image of the respiratory flow rate (IdD) and/or to determine an image of the respiratory volume (IdV) over at least part of over three or four successive given respiratory cycles.

12. The apparatus as claimed in claim 9, wherein the means of determining the moving average make it possible to determine the moving average (ma-IdV) of the image of the respiratory volume of the patient over the n respiratory cycles which preceded at least one given respiratory cycle, with n>10.

13. The apparatus as claimed in claim 12, wherein the means of determining the moving average make it possible to determine the moving average (ma-IdV) of the image of the respiratory volume of the patient over the n respiratory cycles which preceded at least one given respiratory cycle, with n between 15 and 40.

14. The apparatus as claimed in claim 13, wherein the means of determining the moving average make it possible to determine the moving average (ma-IdV) of the image of the respiratory volume of the patient over the n respiratory cycles which preceded at least one given respiratory cycle, with n between 20 and 30.

15. The apparatus as claimed in claim 9, wherein the means of determining at least one cue representative of at least one respiratory flow rate restriction make it possible to subtract a value of moving average (ma-IdV) of the image of the respiratory volume, as determined by the means of determining the moving average, from the value of the area (Acc) of the current consumed corresponding to the image of the respiratory volume (IdV) as determined by the means of determining an image of the respiratory volume (IdV).

* * * * *